US009604955B2

(12) United States Patent
Guo

(10) Patent No.: US 9,604,955 B2
(45) Date of Patent: Mar. 28, 2017

(54) CHEMICAL ENHANCEMENT BY NANOMATERIALS UNDER X-RAY IRRADIATION

(71) Applicant: The Regents of the University of California, Oakland, CA (US)

(72) Inventor: Ting Guo, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/370,733

(22) PCT Filed: Jan. 11, 2013

(86) PCT No.: PCT/US2013/000015
§ 371 (c)(1),
(2) Date: Jul. 3, 2014

(87) PCT Pub. No.: WO2013/106219
PCT Pub. Date: Jul. 18, 2013

(65) Prior Publication Data
US 2014/0371471 A1     Dec. 18, 2014

Related U.S. Application Data

(60) Provisional application No. 61/586,588, filed on Jan. 13, 2012.

(51) Int. Cl.
*G01N 33/00* (2006.01)
*C07D 311/12* (2006.01)
(52) U.S. Cl.
CPC ................. *C07D 311/12* (2013.01)

(58) Field of Classification Search
CPC ................................. C07D 311/12
See application file for complete search history.

(56) References Cited

U.S. PATENT DOCUMENTS

2008/0089836 A1* 4/2008 Hainfeld ............ A61K 49/0428
424/1.11
2010/0034735 A1* 2/2010 Chen .................... A61K 9/5115
424/1.29

OTHER PUBLICATIONS

Misawa ("Generation of reactive oxygen species induced by gold nanoparticles under x-ray and UV irradiations" Nanomedicine: Nanotechnology, Biology and Medicine, Volume & (online published Jan. 14, 2011, accepted Jan. 18, 2011).*

(Continued)

*Primary Examiner* — Sam P Siefke
(74) *Attorney, Agent, or Firm* — Kilpatrick Townsend and Stockton LLP

(57) ABSTRACT

A method for dynamic enhancement of chemical reactions by nanomaterials under hard X-ray irradiation. The nanomaterials were gold and platinum nanoparticles, and the chemical reaction employed was the hydroxylation of coumarin carboxylic acid. The reaction yield was enhanced 2000 times over that predicted on the basis of the absorption of X-rays only by the nanoparticles, and the enhancement was found for the first time to depend on the X-ray dose rate. The maximum turnover frequency was measured at 1 16×10-4 s-1 Gy-1. We call this process chemical enhancement, which is defined as the increased yield of a chemical reaction due to the chemical properties of the added materials. The chemical enhancement described here is believed to be ubiquitous and may significantly alter the outcome of chemical reactions under X-ray irradiation with the assistance of nanomaterials.

19 Claims, 9 Drawing Sheets

(56) References Cited

OTHER PUBLICATIONS

International Preliminary Report on Patentability received for PCT Patent Application No. PCT/US2013/00015, mailed on Jul. 24, 2014, 7 pages.
International Search Report and Written Opinion received for PCT Patent Application No. PCT/US2013/00015, mailed on Apr. 24, 2013, 9 pages.
Barbalace, Kenneth, "Periodic Table of Elements Sorted by Electronegativity (Pauling)", Available at <http://environmentalchemistry.com/yogi/periodic/electronegativity.html>, website last updated on Feb. 22, 2007, 7 pages.
Chauke et al., "Photocatalytic Behaviour of Tantalum (V) Phthalocyanines in the Presence of Gold Nanoparticles Towards the Oxidation of Cyclohexene", Journal of Molecular Catalysis A: Chemical, vol. 355, 2011, pp. 212-128.
International Bureau of Weights, "The International System of Units (SI)", Organisation Intergouvernementale De La Convention Du Metre, 8th Edition, Available at <http://www.bipm.org/utils/common/pdf/si_brochure_8.pdf>, 2006, 186 pages.

\* cited by examiner

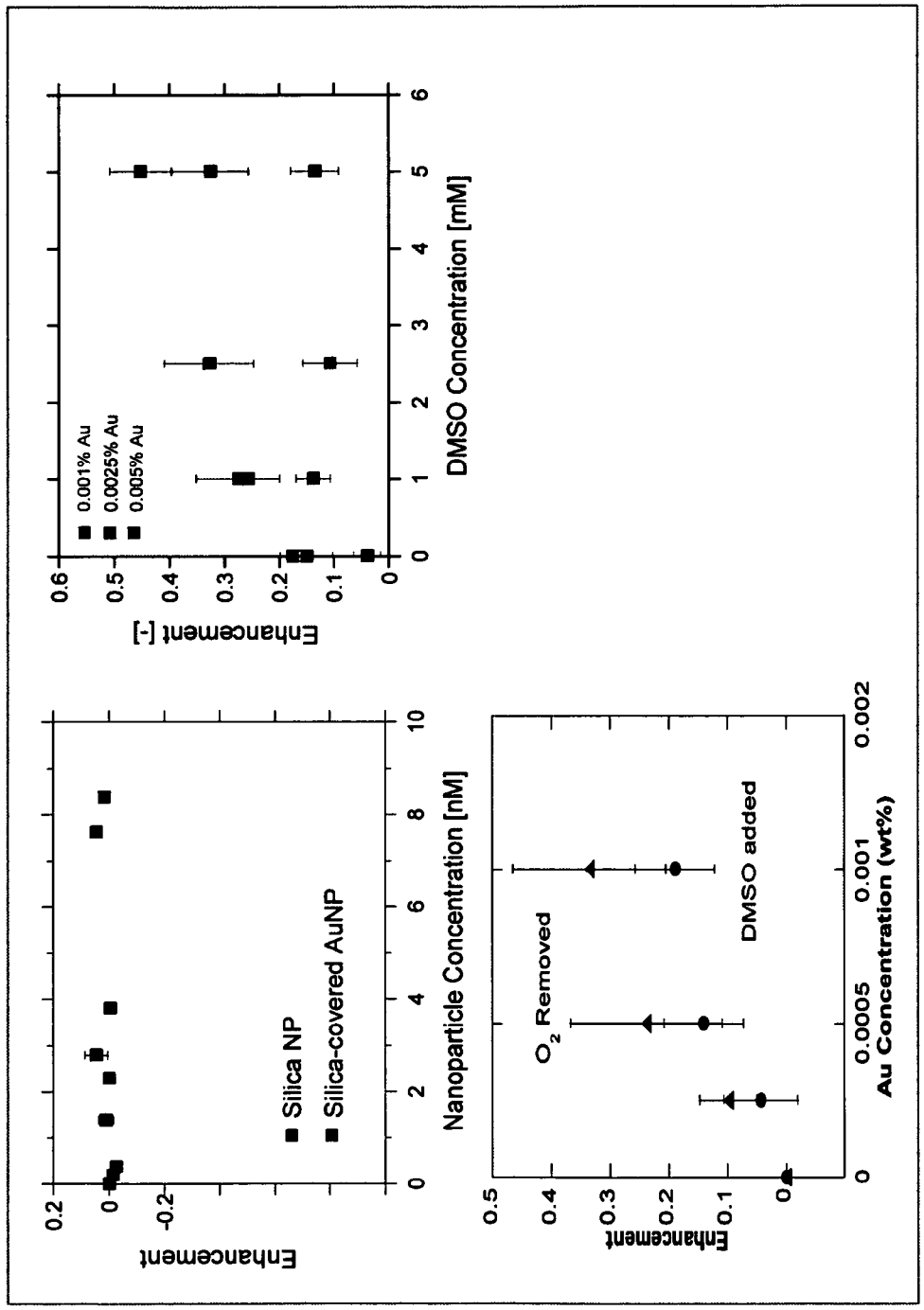
Figure SI-1

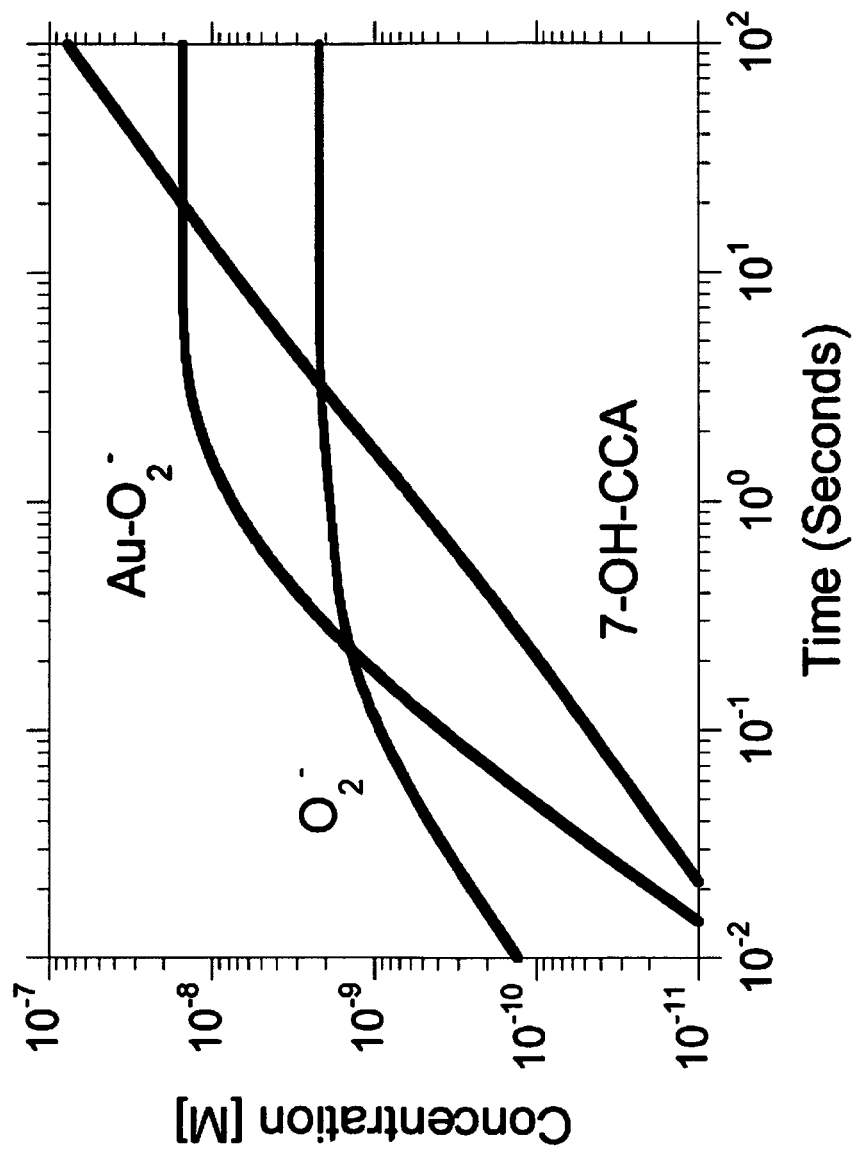
Figure SI-2

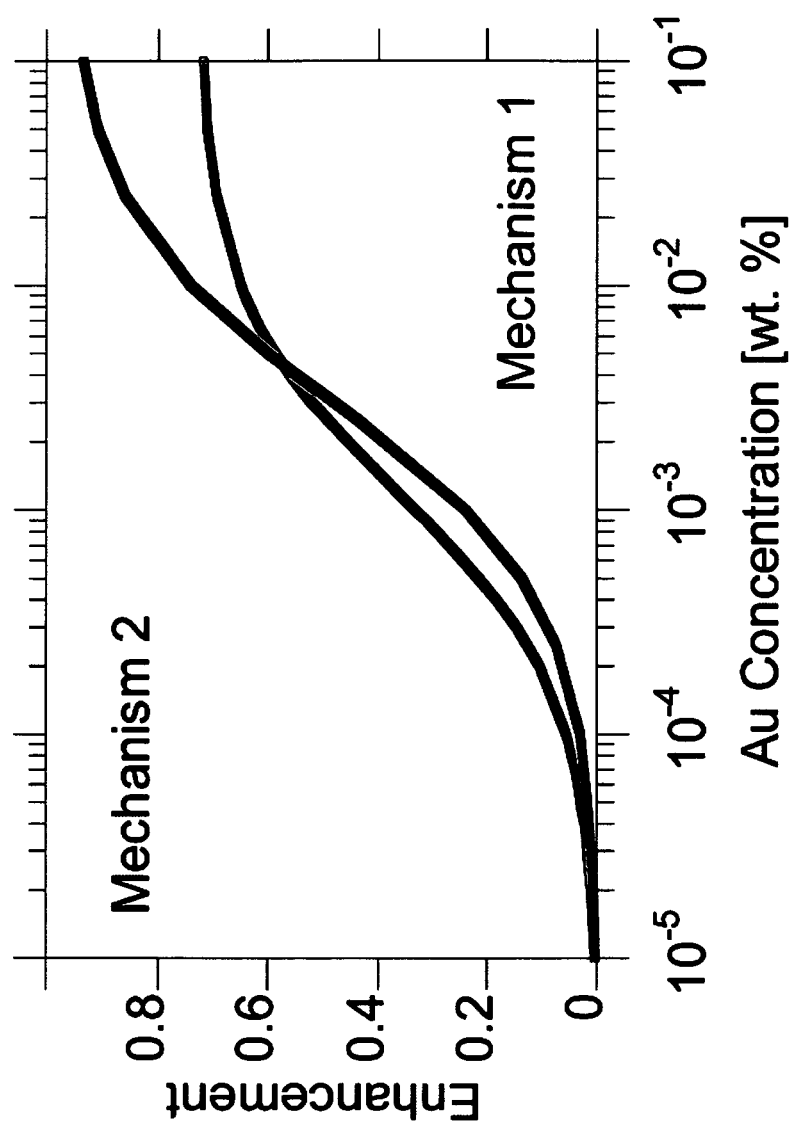
Figure SI-3

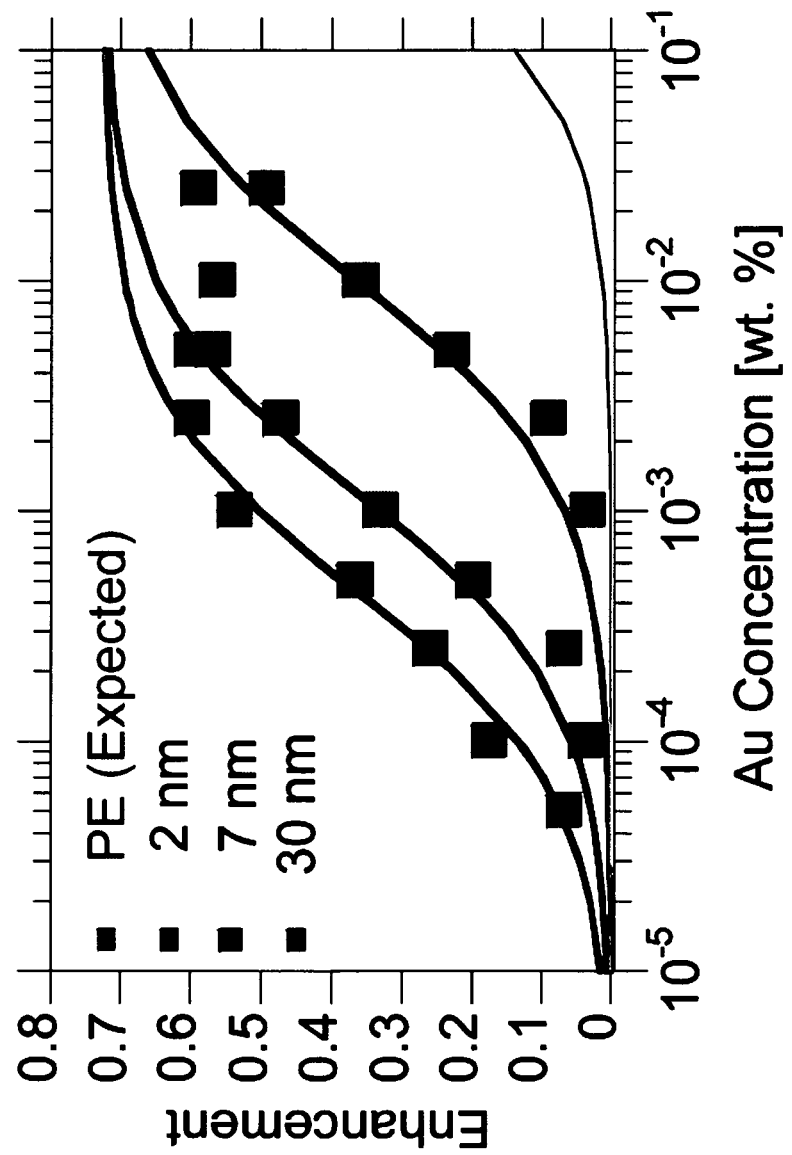
Figure SI-4

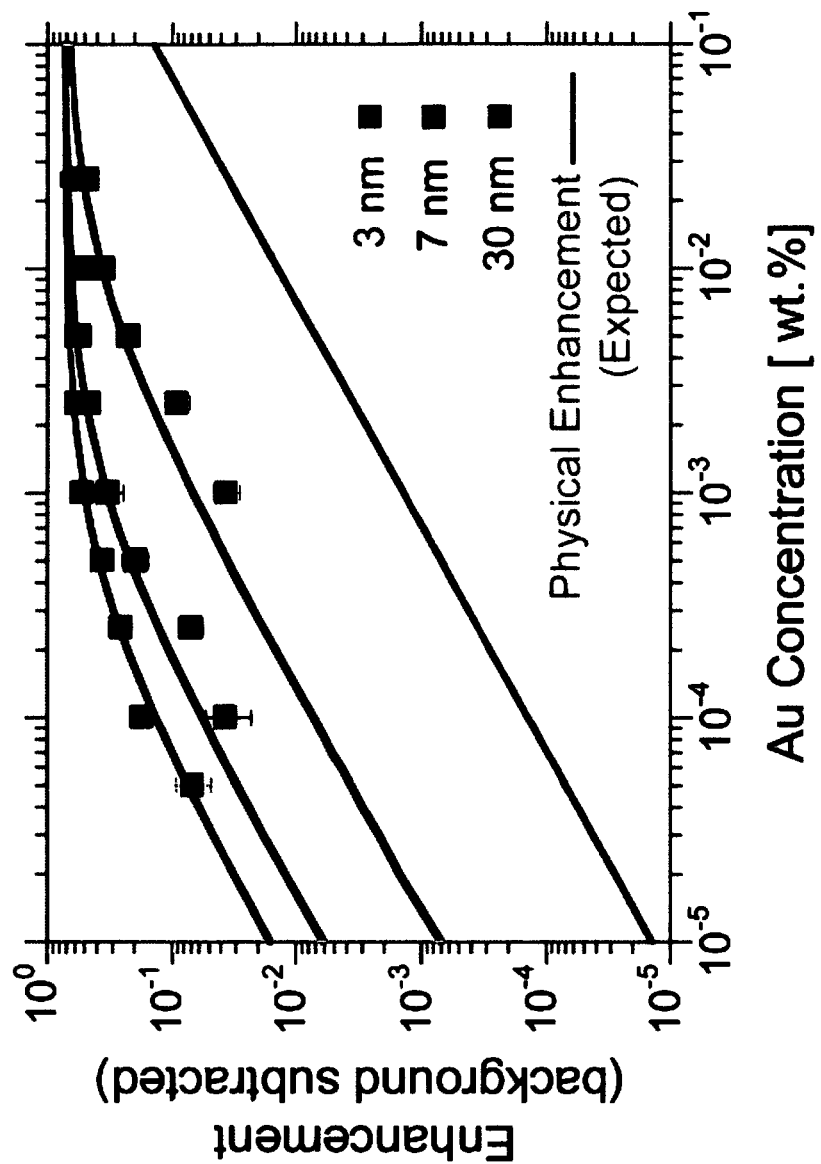
Figure SI-5

CHEMICAL ENHANCEMENT BY NANOMATERIALS UNDER X-RAY IRRADIATION

CROSS-REFERENCE TO RELATED APPLICATIONS

This application is a U.S. National Phase of PCT/US2013/000015, filed Jan. 11, 2013, which claims the benefit of U.S. Provisional Patent Application No. 61/586,588, filed Jan. 13, 2012, each of which is incorporated herein by reference in its entirety for all purposes.

STATEMENT REGARDING FEDERALLY SPONSORED RESEARCH OR DEVELOPMENT

This invention was made with Government support under Grant No. CHE0957413 awarded by the National Science Foundation. The Government has certain rights in this invention.

BACKGROUND OF THE INVENTION

1. Field

The present disclosure relates generally to methods for enhancing chemical reactions, and more specifically to enhancement of chemical reactions through the use of nanomaterials.

2. Description of Related Art

X-ray absorption by materials has been broadly used in imaging, lithography, and treatment since the discovery of X-rays. Nanomaterials, which were widely used as catalysts decades ago, are being intensely explored in many fields, especially biology. The use of previously considered inert nanomaterials such as gold nanoparticles to increase the absorption of X-rays began a few years ago, and many chemical and biological responses have been used to quantify the enhancement.[1,2] Because gold nanoparticles can be catalytically active under suitable conditions,[3-9] it is likely that these nanomaterials may do more than simply enhance the absorption of X-rays in a highly reactive environment such as those created by X-ray radiation. However, all of the observed enhancements to date have been attributed to physical properties of the nanomaterials, i.e., high atomic numbers, leading to increased X-ray absorption and subsequent increased generation of reactive oxygen species (ROS), even though the observed enhancements could be much higher than the values predicted on the basis of the physical enhancement at low loadings (<0.1 wt %) of nanoparticles[1,10] or much lower at high loadings (~1 wt %) of nanoparticles.[11] These disagreements indicate that physical enhancement alone, even taking into account reabsorption of emitted secondary photons and electrons,[12] which is negligible, cannot explain the observed enhancement.

BRIEF SUMMARY

Described herein is a new phenomenon of dynamic enhancement of chemical reactions by nanomaterials under hard X-ray irradiation. The nanomaterials were gold and platinum nanoparticles, and the chemical reaction employed was the hydroxylation of coumarin carboxylic acid. The reaction yield was enhanced 2000 times over that predicted on the basis of the absorption of X-rays only by the nanoparticles, and the enhancement was found for the first time to depend on the X-ray dose rate. The maximum turnover frequency was measured at 116×10-4 s-1 Gy-1. We call this process chemical enhancement, which is defined as the increased yield of a chemical reaction due to the chemical properties of the added materials. The chemical enhancement described here is believed to be ubiquitous and may significantly alter the outcome of chemical reactions under X-ray irradiation with the assistance of nanomaterials.

In one aspect, disclosed herein is the finding that commonly made AuNPs such as those coated with PEG ligands are both catalytically active under X-ray irradiation and can scavenge radicals. The only way to make them inert is to cover them with silica thin films. So this finding enables us to (1) make these nanoparticles inert towards reactions involving ionizing radiation generated reactive oxygen species (ROS); (2) synthesize X-ray dosimetry probing nanomaterials to maximize the conversion of reactants to products; and (3) synthesize nanomaterials that can fiducially detect the amount of ROS. An example of the nanometerials is given in FIG. 4. In this case, the 3CCA molecules will intercept and react with all the OH radicals coming to their way. Silica-coated large AuNPs will not scavenge OH radicals, and the small AuNP surface can still be activated by superoxides, which do not react with 3CCA molecules. This nanosystem can probe chemical enhancement without scavenging OH radicals.

BRIEF DESCRIPTION OF THE DRAWINGS

FIG. SI-1. Surface, oxygen and DMSO effect of chemical enhancement. FIG. 1A). CE from silica-coated gold nanoparticles and silica nanoparticles. Little enhancement is observed. FIG. 1B). DMSO dependency. FIG. 1C). oxygen effects (need to have both the absolute signals and enhancement, which is relative)

FIG. SI-2. Concentrations of free superoxides, adsorbed superoxides, and 7-OH—CCA from 0.01 to 100 Seconds. Dose Rate is set at 3.3 Gy/min. AuNPs concentration is set at 0.01 wt. %, and the size is 7 nm. The result shows that superoxide concentration has reached equilibrium after 10 seconds has elapsed since the start of irradiation.

FIG. SI-3. Simulated enhancement as a function AuNP concentration. Mechanism 1 (red) is described in the text, which is activated by superoxide generated from X-rays. Mechanism 2 is catalytic conversion of superoxide to OH radicals. The magnitude of the enhancement due to mechanism 2 is higher than 1, which agrees well the experimental values. Mechanism 2 could not duplicate the dose rate dependency results.

FIG. SI-4. Simulated enhancement as a function AuNP concentration for three different sizes of AuNPs of 2, 7, and 30 nm. Reactions from 3-CCA to 7-OH—CCA through superoxide activated AuNPs are assumed. Also shown is the physical enhancement (PE), which does not become measurable (i.e., greater than 10% enhancement) until the wt. % is above 0.1%.

FIG. SI-5. Theoretical physical enhancement versus experimental data. The enhancement values shown here are background subtracted. The experimental values were obtained at 3.3 Gy/min, which were only 25% of the maximum enhancement of 200%. The observed maximum enhancement (obtained at 20 Gy/min) is over 2000 times greater than the theoretically predicted values between 0.1 and 1 ppm of Au in water.

DETAILED DESCRIPTION

The following description sets forth exemplary methods, parameters and the like. It should be recognized, however, that such description is not intended as a limitation on the scope of the present disclosure but is instead provided as a description of exemplary embodiments.

Described herein is new concept, chemical enhancement, which is enabled by both the radiation-generated ROS and the surface of the nanomaterials. The concept discovered here may also be useful in applications such as energy production, nuclear waste processing, radiation chemistry, chemical synthesis, radiotherapy, catalysis, sensing, nanotoxicity, and nanomedicine.

Figure 1:
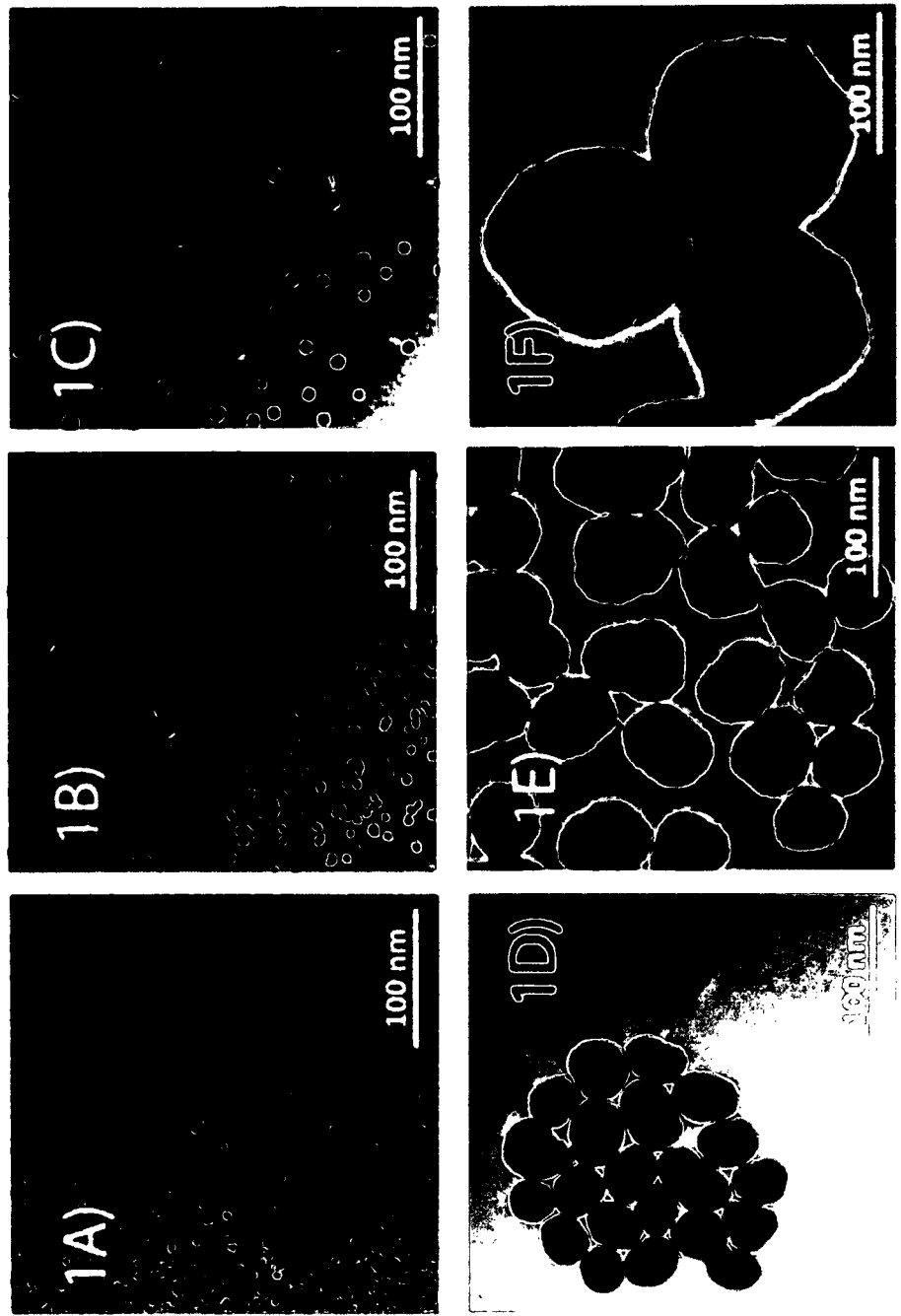
FIG. 1. TEM images of (A) 1.7 nm PtNPs; (B-D) 3, 7, and 30 nm AuNPs; (E) silica NPs (40 nm); and (F) silica-coated AuNPs (72 nm Au core, 29 nm thick silica shell).
Figure 2:
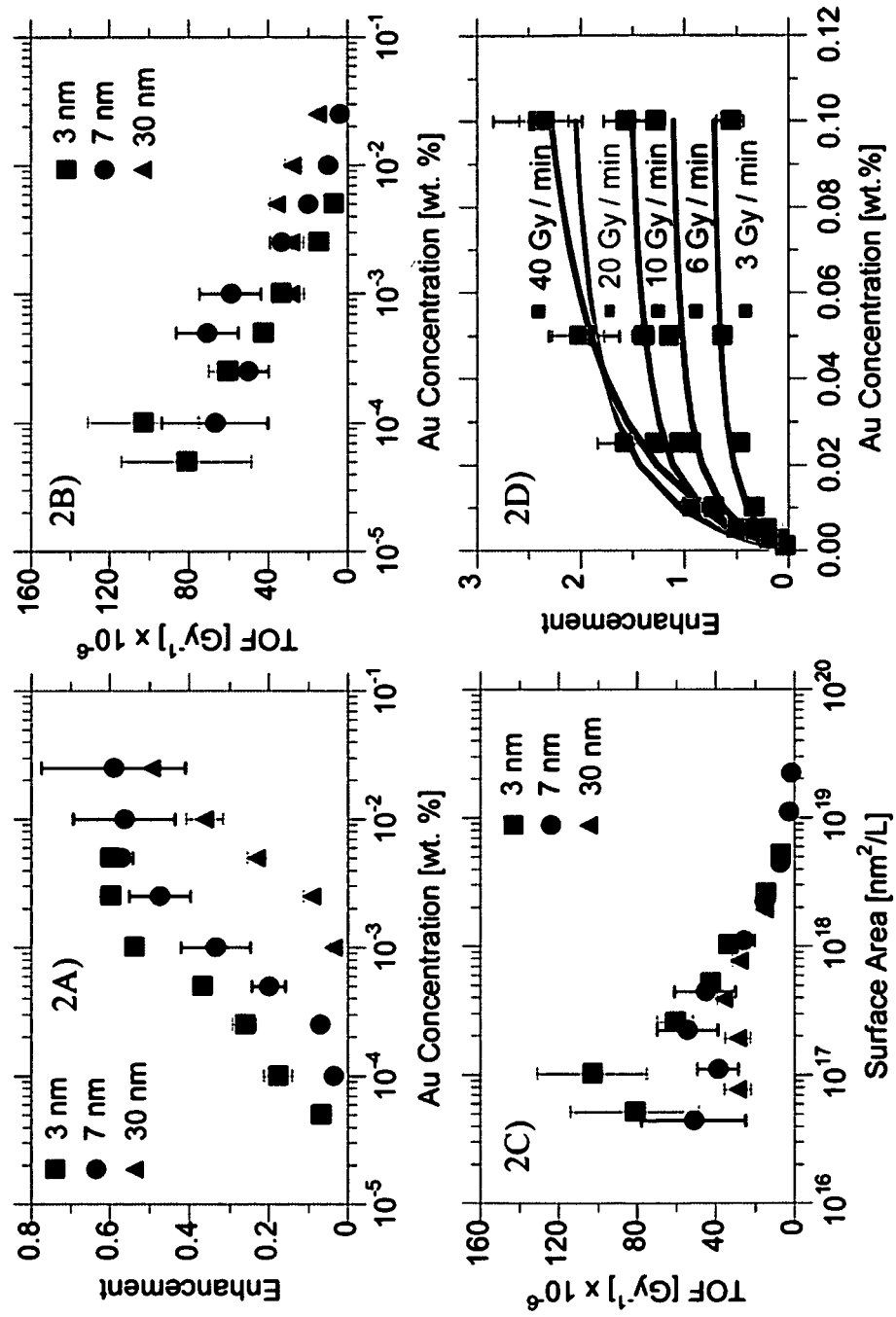
FIG. 2. Chemical enhancement results. (A) Enhancement as a function of AuNP concentration for the three sizes of AuNPs. Enhancement was observed below 1 ppm. (B) TOF for these three sizes of AuNPs. (C) TOF as a function of the total surface area. (D) Dose rate dependence of the absolute enhancement for 7 nm AuNPs. The experimental data are shown as symbols and the theoretical simulations (see the text) as solid lines. The dose rate dependence reached saturation above 20 Gy/min. The simulations were based on a model proposing that the activity of the AuNPs comes from superoxide produced by X ray radiation.

FIG. 1 shows several nanomaterials synthesized and employed here, including 2.0±0.4 nm platinum nanoparticles (PtNPs), 3.8±1.0 nm (denoted as "3 nm" in the text), 7.0±1.3 nm ("7 nm"), and 35.2±4.9 nm ("30 nm") gold nanoparticles (AuNPs), 53±6.4 nm silica nanoparticles, and nanoparticles having a 72.6±4.6 nm gold core and a 28.8±4.0 nm thick silica shell. FIG. 2A shows the increased production of highly fluorescent 7-hydroxycoumarin 3-carboxylic acid (7-OH—CCA) from hydroxylation of weakly fluorescent coumarin 3 carboxylic acid (3 CCA) as a function of AuNP concentration for the three nanoparticle sizes shown in FIG. 1B-D (3, 7, and 30 nm). The increase is expressed as the enhancement of the yield of 7-OH—CCA caused by AuNPs, which is defined as the ratio of the fluorescence signal of 7-OH—CCA with AuNPs to that without AuNPs minus 1. Thus, an enhancement value of 0 means no increase to the yield, and an enhancement value of 1.0 means a 100% increase. The lowest concentration to observe a 10% enhancement was less than 0.5 ppm or 20 nM for the 3 nm AuNPs, 3 ppm or 2.4 nM for 7 nm AuNPs, and 25 ppm or 0.15 nM for 30 nm AuNPs. Because the reaction is used as a dosimetry reaction, naturally such an enhancement would be interpreted as an increase in OH. production, which would be incorrect because AuNPs actually played an active and chemical role. As the amount of AuNPs in solution increased to >0.1 wt %, which is the value needed to generate ~10% physical enhancement (PE) (see below), the experimentally measured enhancements started to decrease and even became negative (i.e., antienhancement; data not shown), which implies that these nanoparticles or their surfactants begin to scavenge OH. at high enough AuNP or PtNP concentrations. This scavenging process may be the cause of the observed low enhancement at high loadings of nanoparticles. However, scavenging is negligible at sufficiently low concentrations (<0.1 wt %) of AuNPs, as shown in FIG. 2. The enhancements reached a maximum of 0.6 (60%) at an X ray irradiation dose rate of 3.3 Gy/min. If this is a catalytic reaction, then on the basis of FIG. 2A, the traditionally defined parameter of turnover frequency (TOF), which is the number of chemical reactions catalyzed by a surface atom in nanoparticles per second, can be calculated. FIG. 2B shows that the TOF reached the highest values at the lowest concentrations for each of the three sizes of nanoparticles and then gradually decreased as the concentration of nanoparticles increased. Such a decrease in TOF with increasing total surface area suggests that there is a limiting reagent other than the surface area of AuNPs. On the basis of the data shown in FIGS. 2A,B over a large range of concentrations, it appears that there is a size dependence. The prominence of this feature subsided when the TOF data were plotted as a function of the total surface area (FIG. 2C), although the 3 nm AuNPs still seemed to be better than the 30 nm AuNPs by a factor of 2 at the lowest surface areas. The TOF reached a plateau at the maximum value of nearly 1×10−4 s−1 Gy−1 at a dose rate of 3.3 Gy/min for 3 nm AuNPs with minimum total surface areas. This weak size independence, which exists for several catalytic systems,[14] is characteristically different from the catalytic properties of small AuNPs, indicating that the mechanism of enhancement is different from that causing the oxidation of CO by small AuNPs on substrates.

To test whether the observed activity truly originated from the surface of gold and not from poly(ethylene glycol) (PEG) or other ligands covering the AuNPs or even just any type of nanoparticle, we synthesized and employed pure silica nanoparticles and silica shell covered AuNPs (FIGS. 1E,F). There was almost no scavenging or enhancement at already high nanoparticle concentrations. PEG covered silica nanoparticles were also tested, and no enhancement was observed, proving that enhancement does not happen for nanoparticles in general [see FIG. SI 1 in the Supporting Information (SI)]. This result also reconfirmed that previously claimed re emission or absorption of secondary X rays did not cause the enhancement.[12] On the other hand, for an equal amount of AuNPs, there was measurable enhancement, as shown in FIG. 2A. This proves that the enhancement observed in FIG. 2A-C was due to the surface gold atoms of the AuNPs and not to the bulk gold atoms or surface atoms of nanoparticles in general. We also synthesized and employed several other nanoparticles, including Ag, Pt, CdTe, and TiO2 nanoparticles. PtNPs (2 nm) covered with poly(vinylpyrrolidone) (PVP) ligands showed similar enhancement as AuNPs. On the other hand, no enhancement was observed over a large span of concentrations for 15 nm AgNPs, suggesting that a plasmonic phenomenon is not the cause of the enhancement. 4 CdTe nanoparticles (3 nm) were also synthesized and used, and no enhancement was detected at a dose rate of 3.3 Gy/min. Large band gap semiconductor TiO2 nanoparticles alone under X ray irradiation did not cause enhancement either.

We employed excessive amounts of sodium azide, sodium nitrate, superoxide dismutase (SOD), and ascorbic acid to determine the chemical species responsible for the enhancement. Sodium azide was used to scavenge singlet oxygen preferentially, and the enhancement was unchanged with the addition of up to 1 mM sodium azide, proving that singlet oxygen was not responsible for the enhancement. On the other hand, 0.5 mg/mL SOD or 0.5 mM ascorbic acid quenched the enhancement. Ascorbic acid scavenges OH, superoxide, and singlet oxygen, whereas SOD removes only superoxides effectively. These results suggest that the enhancement relies on superoxides. Sodium nitrate aqueous solution was employed to test the role of solvated electrons, and no detectable changes were found.

On the basis of these investigations, we hypothesize that weakly electronegative metal surfaces free of oxides, such as those of AuNPs or PtNPs, may be necessary for the enhancement observed here.[4] Superoxides are also required; their role may be to transfer electrons to the AuNPs or PtNPs to make them anionic, allowing OH radical adduct inter mediates 3 OH CCA. to react on the surface to form 7 OH CCA either sequentially or simultaneously. If these hypotheses are true, then the enhancement should increase as a result of simultaneously increasing the concentration of intermediates and the total surface area of the nanomaterials. This could be done with more intense X ray sources and greater nanoparticle concentrations. FIG. 2D shows the results of enhancement measurements using a more intense microfocus X ray source. The dose rate measurements showed that the enhancement was much improved at higher dose rates and high AuNP concentrations, eventually reaching 200% or 2 fold enhancement at 20 Gy/min with 0.1 wt % 7 nm AuNPs (square symbols for experimental data). The solid lines are theoretically predicted responses (see below). These results show that enhancement is dose rate dependent at high AuNP concentrations and suggest that the enhancement processes must involve species such as superoxides that are generated by X ray radiation.

Figure 3:
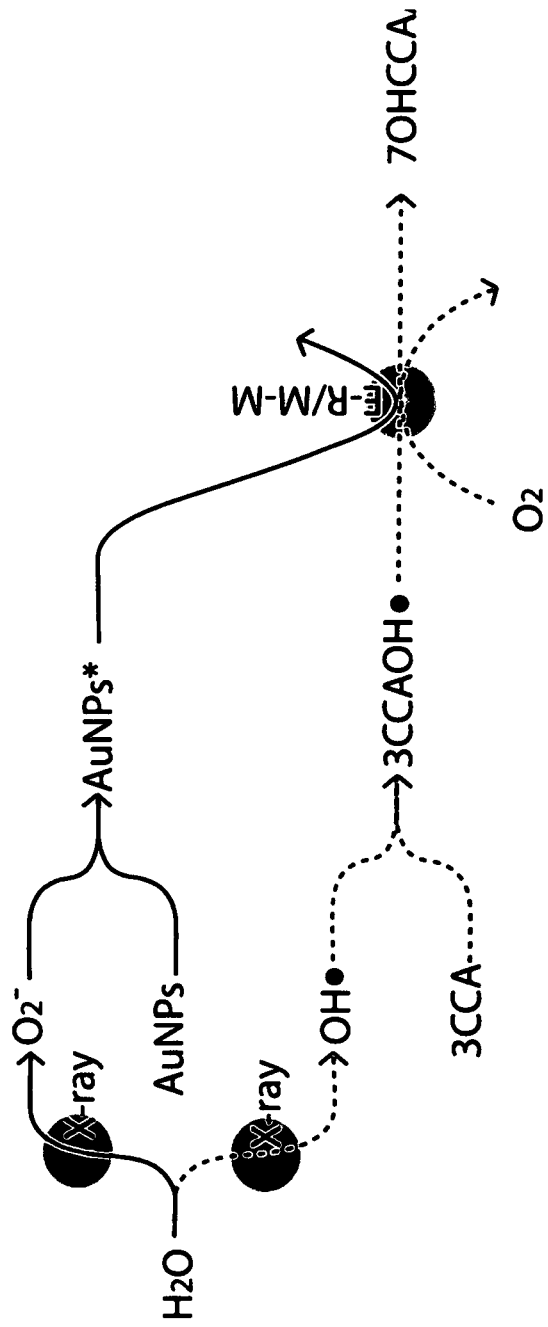
FIG. 3. Proposed mechanisms for chemical enhancement. The proposed mechanism is a combination of the Michaelis-Menten (M-M) and Eley-Rideal (E-R) mechanisms. Two possible reaction pathways are shown: pathway 1 (dashed lines) is the previously established mechanism of formation of 7 OH CCA, and pathway 2 (solid lines) displays the proposed superoxide activated AuNP pathways. Pathway 2 employs OH. produced from AuNPs, but OH. from water would also be possible. O2, superoxide (O2-), OH., 3 CCA, 3 OH CCA. (radical), 7 OH CCA (the product), and AuNPs are shown.
Figure 4:
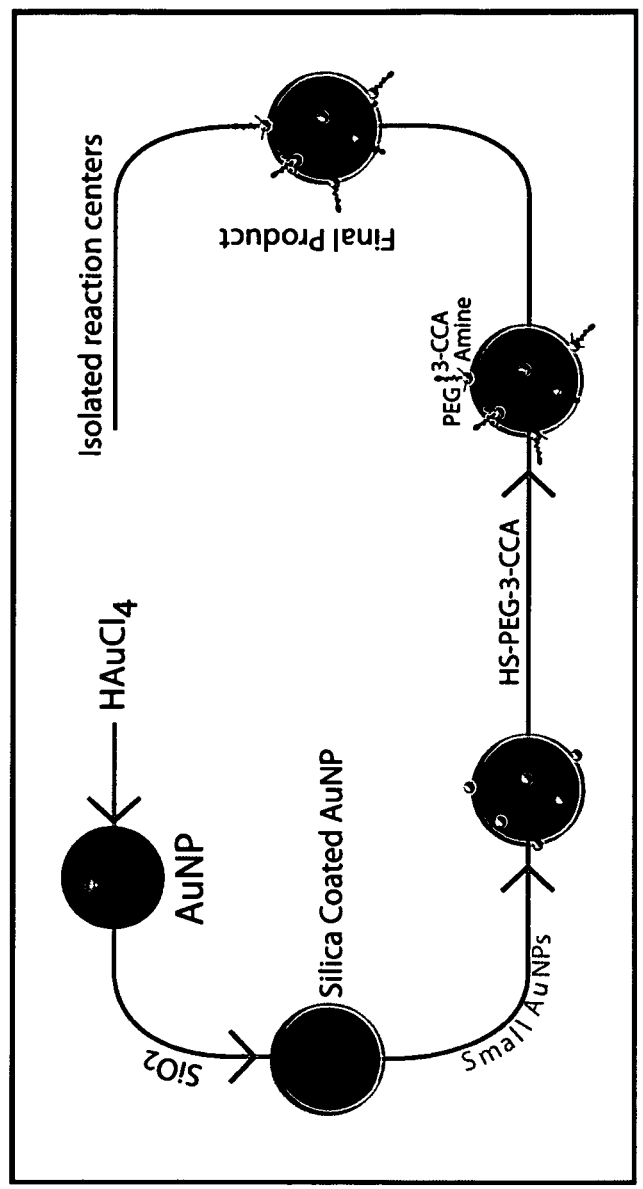
FIG. 4 shows an example nanomaterial of the disclosure.

The observed experimental data can be explained by reactions of radical intermediates 3 OH CCA. with super oxide activated AuNPs or PtNPs. FIG. 3 shows the new reaction pathway involving activation of the surface atoms in AuNPs by X ray radiation generated superoxides (solid lines). The originally proposed pathway in the literature is also shown (dashed lines).[15] The new pathway can be considered as a combination of at least two well-known catalytic reaction mechanisms. The radical intermediate 3 OH CCA. can be regarded as the substrate in the traditional enzyme kinetics described in the Michaelis-Menten (M-M) framework, where AuNP-superoxide (AuNP—$O_2$—) would be the designated enzyme. However, it is possible that an AuNP could become negatively charged upon reaction with a superoxide, and the negatively charged AuNP would enhance the reaction between 3 OH CCA. and one of the O2 molecules around the negatively charged AuNP (shown in FIG. 3) to form 7 OH CCA. This deviates from the original M-M picture but resembles a process described as the Eley-Rideal (E-R) mechanism because the reacting oxygen molecule comes to the surface of the AuNP to initiate the reaction. This combination hence represents a new mechanism that makes the enhancement dose rate dependent. Although 3 OH CCA. may react with $O_2$ in water and the complex may migrate to the surface of AuNPs, this is unlikely because the lifetime of 3 OH CCA-O2 is fairly short.[16] The proposed mechanism is different from another previously proposed mechanism that suggests oxygen may interact with the gold surface to form superoxides;[17] if AuNPs could form superoxides without radiation as found in previous studies,[17] then the enhancement would be dose rate independent. We theoretically modeled the enhancement by establishing the rate equations for AuNPs, DMSO, O2, O2— and the dose rate (see eqs 1-6 in the SI). The AuNP concentration dependence shown in FIG. 2A was reproduced, closely resembling that obtained based on the Langmuir-Hinshelwood formula with the modification that O2 can be any of those around the AuNPs and not necessarily the adsorbed superoxide itself.18 The solid lines in FIG. 2D show the theoretically modeled results of the dose rate calculation, which agree with the experimental data. In addition, the concentration dependence and nanoparticle size effect were also duplicated using this model (see FIGS. SI 3 and SI 4).

The chemical enhancement (CE) of the effect of X ray radiation described here requires the activation of nanomaterials by superoxides produced under X ray irradiation. Therefore, we call it dynamic CE. CE is different from physical enhancement (PE), which is defined as the increased absorption of radiation that leads to increased generation of ROS such as superoxides, OH., and singlet oxygen as a result of the introduced materials under irradiation. PE hence enhances the X ray absorption and therefore the energy deposition.[19] Many examples exist. For instance, AuNPs were employed to increase the cleavage of DNA strands through increased absorption of X rays.[2] Nanoporous gold has been shown to enhance radiolysis of water.[20] Several recent experiments employed AuNPs for their PE property and observed enhanced damage to biological samples.[21-23] Theoretical works have also been carried out to explain the results in terms of the enhanced energy deposition from the added nanomaterials.[19,24-26] PE can be further divided into two categories. Average or remote PE, which we call type 1 PE, creates uniform enhancement in solution. A general rule of thumb is that adding 1 wt % gold (relative to water in the sample) creates ~140% increase in energy deposition. The observed CE for 3 nm AuNPs at 4×10−5 wt % (FIG. 2A) is hence 2000 times the predicted type 1 PE (FIG. SI 5). Type 2 PE, a nanoscale or local physical enhancement, can be effective only when two conditions are simultaneously met: (1) the probe molecules (e.g., DNA) must be placed within nanometers of the nanomaterial (e.g., AuNPs) and (2) scavengers must be present to reduce the contribution of OH. from surrounding water.[19] However, neither condition was met here. Both types of PE can depend on the X ray energy.[27] Another possibility is that superoxides may be converted to OH. and hydroperoxyl radicals by AuNPs (see the SI). However, the amount of OH. produced this way is considerably less than that produced from radiation of water, and only a very small amount of hydroperoxyl radicals exist at pH 7.0.[28] Furthermore, this mechanism could not reproduce the observed dose rate dependence shown in FIG. 2D. As a result, both types of PE could not explain the enhancements measured here, and there is a negligible increase in ROS due to the introduction of nanoparticles. We hence conclude that the observed enhancement is solely caused by the increased conversion of intermediates to the products occurring on the surface of AuNPs or PtNPs.

The presented results show that only a small amount of AuNPs can cause significant changes in the outcome of radiation experiments. The proposed radiation activated dynamic CE can also explain the previously observed enhancement in several studies in which a ~50% increase in the damage to biological samples was observed when <0.01 to 0.1 wt % AuNPs (uptake) was employed.11,29,30 The observed enhanced damage could not be explained by PE, which at best could account for only a small fraction of the damage. On the other hand, on the basis of the work presented here, CE should be on the order of 50% at those AuNP concentrations, and the CE discovered here remains high in the presence of radical scavengers such as those abundant in cells. It is also possible that CE may lead to more complicated biological enhancement, so the concept of CE may play an important role in understanding reactive environments such as cells where radiation generated and naturally existing intermediates and ROS activated nanomaterials are abundant, which could be crucial for understanding nanotoxicity under radiation.

Supplementary Information

Experimental and Theoretical Methods
1. Synthesis
  1.1. Synthesis of Gold Nanoparticles (AuNPs)
    a. Synthesis of 3-nm AuNPs 3-nm AuNPs were prepared following Qu's method.[1] Briefly, 0.5 ml of 1 M NaOH and 1 mL of tetrakis-hydroxymethyl-phosphonium chloride (THPC) solution (prepared by addition of 12 μL aqueous 80% THPC solution to 1 ml Mili-Q water) were added into a 45 mL aliquot of Mili-Q water.[2] The mixture was vigorously stirred for 5 minutes. 2.0 mL of aqueous 1% $HAuCl_4$ was quickly added to this stirring solution. The color changed to dark brown immediately indicating the formation of AuNPs.

b. Synthesis of the 7-nm AuNPs 69.2 μL of gold(III) chloride solution (30 wt. % in dilute HCl) was added to 10 mL of water. Then a 10 mL aqueous solution of 58.8 mg sodium citrate was added quickly to the solution. After 5 minutes, a solution of 1.7 mg $NaBH_4$ in 20 mL of water was added under rapid stirring. After 45 minutes of reaction, a 2-mL solution containing 10 mg thiolated PEG (thiol-PEG, 2000 MW) was added under a reduced stirring speed. In the case of the synthesis of mercaptopropionic acid (MPA) AuNPs, the thiol-PEG was replaced by MPA. The functionalization proceeded overnight and the solution was concentrated to 1 wt. % Au with rotary evaporation and purified by centrifugal filtration at 6000 rpm for 10 minutes (Amicon Ultra-15 Centrifugal Filter Unit, 10,000 MWCO). The stock solutions were protected with argon after each usage. The concentration was verified by atomic absorption (AA).

c. Synthesis of 30-nm AuNPs

The 30-nm AuNP was synthesized using the Turkevich method.[3] Briefly, 50 μL of gold(III) chloride solution was added to 150 mL of water in a 250 mL 2-neck round-bottom flask. The solution was heated under reflux until boiling and then 4 mL of a 1% sodium citrate was quickly injected under stirring. After 15 minutes, the flask was cooled to room temperature and 13.8 mg of thiol-PEG in 2.8 mL of water was added and the mixture was left reacting overnight. The solution was purified using the previous procedure.

1.2. Synthesis of the Silica Nanoparticles/Silica-Covered AuNPs
    a. 40-nm Silica Nanoparticles (SNP):

The synthesis was based on a modification of Stober's method as reported by Thomassen et al.[4] 540 μL of Milli-Q water and 898 μL of $NH_4OH$ were added to 40 mL ethanol solution stirring at approximately 400 rpm. The mixture was stirred for 10 minutes before adding 886 μL of TEOS solution in a dropwise manner. The solution was then stirred for 48 hours. When the reaction completed the initial colorless solution became milky white. To purify, the solution was centrifuged at 7230 rpm for 30 minutes, the supernatant was discarded and the precipitate was resuspended in ethanol using an ultrasonicator probe, and this process was repeated three times. Finally the silica nanoparticles can be suspended in water or ethanol as required. The wt. % of silica in the final suspension was determined by completely drying 1 mL of the silica sol in a scintillation vial and obtaining the mass by difference.

b. PEG Coating of the SNPs:

The coating was carried using a modification of the method reported by Gref et al.[5] 5 mg of m-PEG-silane solution was added to 15 mL of ~3% silica sol in ethanol and reacted for 2 hours at 80° C. Ethanol was periodically added to prevent complete evaporation. An extra charge of m-PEG-silane (5 mg in 2 mL water) solution was added to the solution and the reaction continued for two more hours with periodic addition of ethanol to prevent complete evaporation. After 2 hours 30 mL of ethanol was added and the cooled solution was centrifuged at 7230 rpm for 30 minutes. The supernatant was discarded. This process was repeated twice by redispersing the precipitate in ethanol using an ultrasonicator probe to remove the excess unreacted PEG. Finally the precipitate was dispersed in water. The aqueous solution of PEGylated SNPs precipitated with 1 M HCl solution, whereas that of pure SNP does not. The wt. % of PEGylated SNPs in the solution was determined the same way as for SNPs.

c. Thin Silica-Coated AuNPs

The silica coated the AuNPs was performed using a modified procedure based on the method reported by Fernández-López et al.[6] To a vigorously stirring 10 mL 0.5 mM aqueous solution of citrate or cetyltrimethylammonium bromide (CTAB) stabilized AuNPs, 1 mL of freshly prepared 0.12 mM aqueous solution of m-PEG-SH (M.W. 2000) was added and allowed to react for 30 minutes. The solution was centrifuged twice to remove excess unreacted m-PEG-SH. The precipitate was redispersed in 2 mL ethanol. 1915 μL of Milli-Q water, 1930 μL of ethanol and 155 μL of ammonia solution were added to the vigorously stirring 2 mL PEGylated AuNP solution and the solution was allowed to react for 2-4 minutes followed by dropwise addition of 2 mL 4 mM tetraethoxysilane (TEOS) solution in ethanol. The total volume of the solution was then made up to 10 mL by adding 2000 μL of ethanol. After 5 minutes an additional charge of 11 μL 80% TEOS solution was added and the solution was allowed to react via vigorous stirring for 2 hours. The solution was purified by centrifugation and redispersed in water.

1.3. Synthesis of 2-nm Platinum Nanoparticles

The procedure was given by Somorjai et al.[7] Briefly, 1.7 nm Pt particles were made by adding NaOH solution (12.5 mL, 0.5 M) in ethylene glycol to a solution of $H_2PtCl_6 \cdot H_2O$ (250 mg) in 12.5 mL of ethylene glycol. The mixture was heated at 433 K for 3 hours under bubbled nitrogen gas. After reaction, particles were precipitated by adding 1 mL of 2 M HCl and dispersed in ethanol containing 12.2 mg of PVP (MW 29,000)

1.4. Synthesis of Silver Nanoparticles (AgNPs):
    a. Citrate-Capped AgNPs

The synthesis was adopted from Jin et al.[8] 0.0017 g $AgNO_3$ (Sigma-Aldrich, >99.999%) was dissolved in 100 mL water in a 250 mL round-bottom flask and heated to boiling under vigorous stirring. After 2 minutes of boiling, 10 ml and 35 mM aqueous solution of sodium citrate (Sigma-Aldrich, ACS Reagent >99.0%) was quickly added to the vigorously stirring solution of $AgNO_3$. Within a 2-4 minutes the solution turned yellow, which indicates the formation of AgNPs. The solution was allowed to continue boiling for an additional 6 minutes after which it was cooled in an ice-water bath and the magnetic stir bar was removed.

b. Bare AgNPs:

The method was adopted from Solomon et al.[9] To a 30 mL of 2.0 mM sodium borohydride (Acros Organics, 98%) aqueous solution chilled in an ice bath for 5 minutes under vigorous stirring, a 10 mL of 1.0 mM aqueous solution of AgNO$_3$ (Sigma-Aldrich, >99.999%), previously chilled in an ice-water bath for 5 minutes, was added slowly in a dropwise manner. After addition of approximately 3-4 mL of aqueous AgNO$_3$ the solution turned yellow, indicating and the formation of AgNPs which became bright yellow after complete addition of 10 mL aqueous AgNO$_3$.

1.5. Synthesis of CdTe Quantum Dots

The procedure was according to Zhong et al.[10] Briefly, 50.8 mg of tellurium metal and 37.8 mg of NaBH$_4$ was put in a 25 mL 2-necked flask and the air was vacuumed off and replaced with nitrogen. 10 mL of water was injected with a syringe and the mixture was stirred for 30 minutes at 80° C. to produce NaHTe. Concurrently, 0.2 mmol of Cd precursor and 0.4 mmol of MPA was added to a 40 mL solution. The pH of the solution was made to pH 10 by adjusting with 1 M NaOH. Then the air was extracted and filled with Argon using the same technique as above. 2 mL of the NaHTe solution was added through a syringe into the Cd solution at room temperature. Then the solution was refluxed at 100° C. under Ar protection. After 10 minutes, the solution is allowed to cool to room temperature.

2. Experimental Protocol 2.1. Preparation of 3-coumarin-carboxylic acid (3-CCA) Solution A 20 mM 3-CCA (Sigma-Aldrich, 99%) solution dissolved in 80 mM equimolar phosphate buffer in 10 mL of Millipore water was gently heated and stirred in a sealed flask until dissolution. After cooling, an addition of 14 µL of DMSO yielded a 20 mM 3-CCA/100 mM DMSO solution. The solution was diluted 10 times with 80 mM phosphate buffer to produce a stock solution of 2 mM CCA/10 mM DMSO.

2.2. Preparation of Samples for Radiation Experiments

In a cell culture plate (Falcon, 24 wells), equal volume of water and the previously prepared stock solution were mixed together to result in a 300 µL of a 1 mM 3-CCA/5 mM DMSO sample. Similarly, an AuNP solution was mixed with the 3-CCA solution in an identical fashion. Both samples were placed in a BD Falcon 24-well Multiwell plate and placed in a HP Faxitron Model 4385SA to irradiate for 30 minutes at 100 kVp at the dose rate of 3.3 Gy/min. The dose rate was calibrated using Fricke dosimeter.[11] For dose rates from 6-40 Gy/min, the sample was irradiated for a total of 100 Gy using a microfocus X-ray source (L9631, Hamamatzu).

2.3 Treatment of Samples after Irradiation

Afterwards, the solution was diluted until the absorbance of the AuNPs no longer caused fluorometric interference. In the case where the concentration of gold was too high to obtain a reasonable signal-to-noise ratio, the solution was filtered by centrifugation at 6000 rpm for 15 minutes (Amicon Ultra-15 Centrifugal Filter Unit, 10,000 MWCO).

2.4. Fluorometric Analysis

The resulting solution was subjected to quantitative fluorometric analysis at an excitation wavelength of 395 nm and emission wavelength of 442 nm (FluoroMax-P, HORIBA Jobin Yvon). A calibration was performed to correct for the difference in dosage among the wells. The yield of 7-hydroxy-coumarin-3-carboxylic acid (7-OH—CCA) was determined by comparison with a calibration curve determined by commercial 7-OH—CCA (Anaspec). The method of studying of 3-CCA conversion to 7-OH—CCA under X-ray radiation adopted here was similar to those previously published.[12,13]

2.5. Superoxide Dismutase (SOD)

Superoxide dismutase (Sigma-Aldrich, Specification) was weighed and dissolved in water to make stock solutions. A calculated volume of the stock solutions is then mixed with pre-made 3-CCA/DMSO stock solution to result in 300 µL of a 0.01-0.5 mg/mL superoxide dismutase/1 mM 3-CCA/5 mM DMSO solution. Using the same technique, an identical volume of Millipore water was added to another aliquot of the stock CCA/DMSO solution to make a control sample. The two samples were subjected to radiation at 3.3 Gy/min and then measured using fluorometry as described earlier.

3. Other Experimental Results

FIG. SI-1A shows the results of the SNPs and silica-covered AuNPs radiation enhancement results. No enhancement was observed from either sample. FIG. SI-1B shows the DMSO dependency results, and enhancement increased as a function of DMSO concentration. These results suggested that there was observable enhancement even without DMSO, an outcome different from that observed in an earlier study.[14] Nonetheless, adding DMSO increased the enhancement by more than 2-fold, which was caused by the reduction to the signal from the bulk water acting as the background. Oxygen had a similar effect. Removal of oxygen in water increased the enhancement of AuNPs due to the reduction of the signal from the bulk water, therefore increasing the relative signal intensity from AuNPs. This dependency is shown in FIG. SI-1C. It is worth noting that both signals from the bulk water and from AuNPs were reduced after removing oxygen—just that signal reduction to AuNPS was less than that of water.

4. Theoretical Methodology 4.1. Kinetics a. Catalysis through 3-OH—CCA intermediates by AuNPs The simulation was performed using rate equations and radiation yields given by LaVerne et al. and iterated using the finite difference method up to 100 seconds in timesteps of 100 nanoseconds.[15] The formation and time-evolution of the two dominant species of superoxide and hydrogen peroxide was modeled accordingly. In the simulation, superoxides were allowed to reversibly adsorb onto gold. The adsorbed population reacts with the 3-oh-cca. intermediate to form the product 7-OH—CCA. Since no available data is available for the conversion efficiency of 3-OH—CCA. to 7-OH—CCA, an efficiency of 20% was assumed due to the conversion efficiency of the reaction of a similar adduct, toluene-oh, with dissolved oxygen.[16] We assume an 100% conversion efficiency for the gold-assisted pathway. The adsorption constant was allowed to vary as a function of dose rate to match experimental values as shown in table SI-1 below. We also assume that the superoxide was allowed to react with the 3-OH—CCA. at a rate of 0.75 s$^{-1}$ in order to establish a linear relationship between dose rate and superoxide concentration which translates into a linear relationship between dose rate and enhancement. We assume that hydrogen radical is scavenged by the 3-CCA and do not contribute to the superoxide concentration. FIG. SI-2 shows the concentrations of superoxides, AuNPs-o$_2^-$ complexes, and 3-OH—CCA. intermediates (CCAOH in the equations) as a function of time.

$$CCAOH \text{ Generation Rate} = \text{Generation OH} \frac{k_1 CCA}{k_1[CCA]+k_2[DMSO]} \quad (1)$$

$$\frac{dO_2^-}{dt} = \text{Generation rate } e^- - k_{ad}[AuNP][O_2^-] + k_{des}[AuO_2^-] - k_{scavenging}O_2^- \quad (2)$$

-continued $$\frac{dAuO_2^-}{dt} = k_{ad}[AuNP][O_2^-] - k_{des}[AuO_2^-] - k_{scavenging}AuO_2^- \quad (3)$$

$$CCAOH \text{ Generation Rate} \frac{k_4[AuO_2^-]}{k_4^{\frac{1}{2}}[AuO_2^-] + k_3[O_2]}$$

$$\frac{dOHCCA}{dt} = \frac{\gamma_1(CCAOH \text{ Generation Rate})(k_3[O_2])}{k_4^{\frac{1}{2}}[AuO_2^-] + k_3[O_2]} \quad (4)$$

$$\frac{d\text{enhanced}_{OHCCA}}{dt} = \frac{\gamma_2(CCAOH \text{ Generation Rate})(k_4[AuO_2^-])}{k_4^{\frac{1}{2}}[AuO_2^-] + k_3[O_2]} \quad (5)$$

$$\frac{dH_2O_2}{dt} = \text{Generation } H_2O_2 \quad (6)$$

Constants Used:

| | |
|---|---|
| GENERATION E⁻ = 2.6/100 EV[15] | (HYDRATED ELECTRONS GENERATED BY X-RAYS) |
| GENERATION OH = 2.7/100 EV[15] | (HYDROXYL RADICALS GENERATED BY X-RAYS) |
| GENERATION $H_2O_2$ = 0.7/100 EV[15] | (HYDROGEN PEROXIDE GENERATED BY X-RAYS) |
| $K_{DES}$ = 0.3 $S^{-1}$ | (DESORPTION CONSTANT OF SUPEROXIDE) |
| $K_{SCAVENGING}$ = 0.75 $S^{-1}$ | (REACTION RATE CONSTANT OF $O_2^-$ WITH CCA) |
| $K_1$ = 5.6 × 10⁹ $M^{-1}S^{-1}$[17] | (REACTION RATE CONSTANT OF CCA WITH OH) |
| $K_2$ = 7.1 × 10⁹ $M^{-1}S^{-1}$[18] | (REACTION RATE CONSTANT OF DMSO WITH OH) |
| $K_3$ = 3 × 10⁵ $M^{-1}S^{-1}$ | (REACTION RATE CONSTANT OF CCA-OH WITH $O_2$) |
| $K_4$ = 1 × 10⁹ $M^{-1}S^{-1}$ | (ASSUMED REACTION RATE CONSTANT OF CCAOH WITH AU $O_2^-$) |
| $\Gamma_1$ = 0.2 | (CONVERSION EFFICIENCY OF CCAOH WITH $O_2$) |
| $\Gamma_2$ = 1 | (CONVERSION EFFICIENCY OF CCAOH WITH $AUO_2^-$) |

TABLE SI-1

ADSORPTION RATE CONSTANTS USED IN THE DOSE RATE MODELING

| DOSE RATE (GY/MIN) | $K_{AD}$ ($M^{-1}S^{-1}$).* SIZE = 7 NM |
|---|---|
| 3 | 4.5 × 10⁷ |
| 6 | 2 × 10⁷ |
| 10 | 1.5 × 10⁷ |
| 20 | 1 × 10⁷ |
| 40 | 3 × 10⁶ |

TABLE SI-2

ADSORPTION RATE CONSTANTS USED IN THE SIZE EFFECT MODELING

| SIZE (NM) | $K_{AD}$ ($M^{-1}S^{-1}$)* AT 3 GY/MIN |
|---|---|
| 3 | 3.5 × 10⁷ |
| 7 | 1.5 × 10⁸ |
| 30 | 1.5 × 10⁹ |

*ASSUMED VALUES IN OUR SIMULATION b. Conversion of Superoxides to OH. by AuNPs

An alternative mechanism of catalytically converting superoxide to OH. was simulated as described in the main text with the exception of the following constants:

| | |
|---|---|
| $K_{SCAVENGING}$ = 15 $S^{-1}$ | (REACTION RATE CONSTANT OF $O_2^-$ WITH 3-CCA) |
| $K_{DES}$ = 0 $S^{-1}$ | (DESORPTION CONSTANT OF SUPEROXIDE) |

We assume that $O_2^-$ adsorbs onto the AuNPs and is converted to OH⁻, therefore this system does not have characteristics of an adsorption-desorption isotherm. FIG. SI-3 shows the results of enhancements predicted based on these two mechanisms. Mechanism 1 represents the 3-OH—CCA. intermediates catalytically converted to 7-OH—CCA products, and mechanism 2 represents the increased OH. model. The visible difference is the magnitude of the enhancement. It is also important to point out that Mechanism 2 could not generate the dose rate dependency results shown in FIG. 2D in the main text.

FIG. SI-4 shows the simulated size dependency results and that of the physical enhancement (PE). Adsorption constants $k_{ad}$ were adjusted to fit the size curves, as shown in Table-SI-2. The constants were noticably greater to fit the curves over a much larger concentration range than that shown in FIG. 2D. The size dependency derives from the available surface sites for each size of AuNPs. PE is calculated based on the increased amount of energy deposited in water due to the introduction of the AuNPs. No chemical enhancement is considered.

4.2. Physical Enhancement Simulation

The method of calculation was given in a supplemental in our previous publication. Briefly, the enhancement caused by the increased absorption of ionization radiation by AuNPs was calculated by determining the distribution of photons emitted from our X-ray source as a function of energy. The absorption by AuNPs was calculated using photon absorption cross-sections and the amount of energy deposited in water was compared with a system where AuNPs were absent. FIG. SI-5 shows the comparison between the observed enhancement, which was of chemical nature, and the theoretically predicted enhancement caused by pure physical enhancement (PE), i.e., increase in absorption of X-rays by the added AuNPs. A 2000-time difference exists between these two values at 0.5 ppm 2-nm AuNPs in water under 3.3 Gy/min X-ray irradiation. This shows that that PE could not explain the observed results.

REFERENCES (1) Hainfeld, J.; Slatkin, D.; Smilowitz, H. Phys. Med. Biol. 2004, 49, N309.

(2) Foley, E.; Carter, J.; Shan, F.; Guo, T. Chem. Commun. 2005, 3192.

(3) Haruta, M.; Kobayashi, T.; Sano, H.; Yamada, N. Chem. Lett. 1987, 405.

(4) Garcia, H.; Navalon, S.; de Miguel, M.; Martin, R.; Alvaro, M. J. Am. Chem. Soc. 2011, 133, 2218.

(5) Mirkin, C. A.; Zhang, K.; Cutler, J. I.; Zhang, J. A.; Zheng, D.; Auyeung, E. J. Am. Chem. Soc. 2010, 132, 15151.

(6) Tsukuda, T.; Tsunoyama, H.; Ichikuni, N.; Sakurai, H. J. Am. Chem. Soc. 2009, 131, 7086.

(7) Cao, R.; Cao, R.; Villalonga, R.; Diaz Garcia, A. M.; Rojo, T.; Rodriguez Arguelles, M. C. Inorg. Chem. 2011, 50, 4705.

(8) Lambert, R. M.; Turner, M.; Golovko, V. B.; Vaughan, O. P. H.; Abdulkin, P.; Berenguer Murcia, A.; Tikhov, M. S.; Johnson, B. F. G. Nature 2008, 454, 981.

(9) Hutchings, G. J.; Hughes, M. D.; Xu, Y. J.; Jenkins, P.; McMorn, P.; Landon, P.; Enache, D. I.; Carley, A. F.; Attard, G. A.; King, F.; Stitt, E. H.; Johnston, P.; Griffin, K.; Kiely, C. J. Nature 2005, 437, 1132.

(10) McMahon, S. J.; Hyland, W. B.; Muir, M. F.; Coulter, J. A.; Jain, S.; Butterworth, K. T.; Schettino, G.; Dickson, G. R.; Hounsell, A. R.; O'Sullivan, J. M.; Prise, K. M.; Hirst, D. G.; Currell, F. J. Sci. Rep. 2011, 1, 18.

(11) Chithrani, D. B.; Jelveh, S.; Jalali, F.; van Prooijen, M.; Allen, C.; Bristow, R. G.; Hill, R. P.; Jaffray, D. A. Radiat. Res. 2010, 173, 719.

(12) Misawa, M.; Takahashi, J. Nanomedicine 2011, 7, 604.

(13) Shirahata, S.; Hamasaki, T.; Kashiwagi, T.; Imada, T.; Nakamichi, N.; Aramaki, S.; Toh, K.; Morisawa, S.; Shimakoshi, H.; Hisaeda, Y. Langmuir 2008, 24, 7354.

(14) Qu, Y. Q.; Sutherland, A. M.; Lien, J.; Suarez, G. D.; Guo, T. J. Phys. Chem. Lett. 2010, 1, 254.

(15) Louit, G.; Foley, S.; Cabillic, J.; Coffigny, H.; Taran, F.; Valleix, A.; Renault, J. P.; Pin, S. Radiat. Phys. Chem. 2005, 72, 119.

(16) Bohn, B. J. Phys. Chem. A 2001, 105, 6092.

(17) Ionita, P.; Gilbert, B. C.; Chechik, V. Angew. Chem., Int. Ed. 2005, 44, 3720.

(18) Zhang, Z. Y.; Berg, A.; Levanon, H.; Fessenden, R. W.; Meisel, D. J. Am. Chem. Soc. 2003, 125, 7959.

(19) Carter, J. D.; Cheng, N. N.; Qu, Y. Q.; Suarez, G. D.; Guo, T. J. Phys. Chem. B 2007, 111, 11622.

(20) Renault, J. P.; Musat, R.; Moreau, S.; Poidevin, F.; Mathon, M. H.; Pommeret, S. Phys. Chem. Chem. Phys. 2010, 12, 12868.

(21) Butterworth, K. T.; Coulter, J. A.; Jain, S.; Forker, J.; McMahon, S. J.; Schettino, G.; Prise, K. M.; Currell, F. J.; Hirst, D. G. Nanotechnology 2010, 21, 29.

(22) Sicard Roselli, C.; Brun, E.; Duchambon, P.; Blouquit, Y.; Keller, G.; Sanche, L. Radiat. Phys. Chem. 2009, 78, 177.

(23) Hwu, Y.; Liu, C. J.; Wang, C. H.; Chen, S. T.; Chen, H. H.; Leng, W. H.; Chien, C. C.; Wang, C. L.; Kempson, I. M.; Lai, T. C.; Hsiao, M.; Yang, C. S.; Chen, Y. J.; Margaritondo, G. Phys. Med. Biol. 2010, 55, 931.

(24) Pradhan, A. K.; Nahar, S. N.; Montenegro, M.; Yu, Y.; Zhang, H. L.; Sur, C.; Mrozik, M.; Pitzer, R. M. J. Phys. Chem. A 2009, 113, 12356.

(25) Cho, S. H.; Jones, B. L.; Krishnan, S. Phys. Med. Biol. 2009, 54, 4889.

(26) Kobayashi, K.; Usami, N.; Porcel, E.; Lacombe, S.; Le Sech, C. Mutat. Res., Rev. Mutat. Res. 2010, 704, 123.

(27) McMahon, S. J. J. Phys. Chem. C 2011, 115, 20160.

(28) Zafiriou, O. C. Mar. Chem. 1990, 30, 31.

(29) Roa, W.; Zhang, X. J.; Guo, L. H.; Shaw, A.; Hu, X. Y.; Xiong, Y. P.; Gulavita, S.; Patel, S.; Sun, X. J.; Chen, J.; Moore, R.; Xing, J. Z. Nanotechnology 2009, 20, 37.

(30) Kong, T.; Zeng, J.; Wang, X. P.; Yang, X. Y.; Yang, J.; McQuarrie, S.; McEwan, A.; Roa, W.; Chen, J.; Xing, J. Z. Small 2008, 4, 1537.

REFERENCES—SUPPLEMENTARY INFORMATION

1. Qu, Y. Q.; Porter, R.; Shan, F.; Carter, J. D.; Guo, T., *Langmuir* 2006, 22, (14), 6367-6374.

2. Duff, D.; Baiker, A.; Gameson, I.; Edwards, P., *Langmuir* 1993, 9, (9), 2310-2317.

3. Plech, A.; Kimling, J.; Maier, M.; Okenve, B.; Kotaidis, V.; Ballot, H., *Journal of Physical Chemistry B* 2006, 110, (32), 15700-15707.

4. Martens, J. A.; Thomassen, L. C. J.; Aerts, A.; Rabolli, V.; Lison, D.; Gonzalez, L.; Kirsch-Volders, M.; Napierska, D.; Hoet, P. H.; Kirschhock, C. E. A., *Langmuir* 2010, 26, (1), 328-335.

5. Gref, R.; Luck, M.; Quellec, P.; Marchand, M.; Dellacherie, E.; Harnisch, S.; Blunk, T.; Muller, R. H., *Colloids and Surfaces B-Biointerfaces* 2000, 18, (3-4), 301-313.

6. Pastoriza-Santos, I.; Fernandez-Lopez, C.; Mateo-Mateo, C.; Alvarez-Puebla, R. A.; Perez-Juste, J.; Liz-Marzan, L. M., *Langmuir* 2009, 25, (24), 13894-13899.

7. Song, H.; Rioux, R. M.; Hoefelmeyer, J. D.; Komor, R.; Niesz, K.; Grass, M.; Yang, P. D.; Somorjai, G. A., *Journal of the American Chemical Society* 2006, 128, (9), 3027-3037.

8. Jin, R. C.; Jureller, J. E.; Kim, H. Y.; Scherer, N. F., *Journal of the American Chemical Society* 2005, 127, (36), 12482-12483.

9. Solomon, S. D.; Bahadory, M.; Jeyarajasingam, A. V.; Rutkowsky, S. A.; Boritz, C.; Mulfinger, L., *Journal of Chemical Education* 2007, 84, (2), 322-325.

10. Zhong, X. H.; Gu, Z. Y.; Zou, L.; Fang, Z.; Zhu, W. H., *Nanotechnology* 2008, 19, (13).

11. Klassen, N. V.; Shortt, K. R.; Seuntjens, J.; Ross, C. K., *Physics in Medicine and Biology* 1999, 44, (7), 1609-1624.

12. Louit, G.; Foley, S.; Cabillic, J.; Coffigny, H.; Taran, F.; Valleix, A.; Renault, J. P.; Pin, S., *Radiation Physics and Chemistry* 2005, 72, (2-3), 119-124.

13. Manevich, Y.; Held, K. D.; Biaglow, J. E., *Radiation Research* 1997, 148, (6), 580-591.

14. Carter, J. D.; Cheng, N. N.; Qu, Y. Q.; Suarez, G. D.; Guo, T., *Journal of Physical Chemistry B* 2007, 111, (40), 11622-11625.

15. LaVerne, J. A.; Pastina, B., *Journal of Physical Chemistry A* 2001, 105, (40), 9316-9322.

16. Bohn, B., *Journal of Physical Chemistry A* 2001, 105, (25), 6092-6101.

17. Baldacchino, G.; Maeyama, T.; Yamashita, S.; Taguchi, M.; Kimura, A.; Katsumura, Y.; Murakami, T., *Chemical Physics Letters* 2009, 468, (4-6), 275-279.

18. Jahnke, L. S., *Analytical Biochemistry* 1999, 269, (2), 273-277.

I claim:

1. A method for enhancing a chemical reaction, the method comprising:
   irradiating, with X-rays, a solution comprising:
      a nanomaterial having (1) at least one metal surface, (2) a diameter in the range of 3 nm to 30 nm, and (3) a concentration in the solution of 0.01 to 0.1 weight percent nanomaterial in solution, and
      one or more chemical reactants;
   wherein the irradiation occurs for a period of time sufficient to generate one or more superoxide species and for the one or more chemical reactants to undergo a chemical reaction to yield one or more products, and
   wherein the chemical reaction occurs at a reaction rate that is at least 10% greater than the reaction rate for a chemical reaction under similar conditions, without the presence of the nanomaterial.

2. The method of claim 1, wherein the nanomaterial is a nanomaterial having a weakly electronegative metal surface free of oxides.

3. The method of claim 1, wherein the nanomaterial is a gold or platinum nanoparticle.

4. The method of claim 1, wherein the nanomaterial is a gold nanoparticle.

5. The method of claim 1, wherein the X-ray irradiation is at a dose rate of 3.3 Gy/min to 40 Gy/min.

6. The method of claim 1, wherein the irradiation occurs for period of time sufficient to irradiate with a total dose of 100 Gy of x-ray irradiation.

7. The method of claim 1, wherein the reaction rate is at least 25% greater than the reaction rate for a chemical reaction under similar conditions, without the presence of the nanomaterial.

8. The method of claim 1, wherein the reaction rate is approximately 200% greater than the reaction rate for a chemical reaction under similar conditions, without the presence of the nanomaterial.

9. The method of claim 1, wherein the reaction comprises a hydroxylation reaction.

10. The method of claim 1, wherein one of the one or more chemical reactants comprises coumarin carboxylic acid.

11. The method of claim 1, wherein the nanomaterial comprises a polyethylene glycol ("PEG") ligand coating.

12. A method for enhancing a chemical reaction, the method comprising:
irradiating, with X-rays at a dose rate of between about 3 Gy/min and about 40 Gy/min, a solution comprising:
a nanomaterial comprising a gold or platinum nanoparticle having a diameter in the range of 3 nm to 30 nm, and a concentration in the solution of 0.01 to 0.1 weight percent nanomaterial in solution, and
one or more chemical reactants;
wherein the chemical reaction occurs at a reaction rate that is at least 10% greater than the reaction rate for a chemical reaction under similar conditions, without the presence of the nanomaterial.

13. The method of claim 12, wherein the irradiation occurs for a period of time sufficient to irradiate with a total dose of 100 Gy of x-ray irradiation.

14. The method of claim 12, wherein the method causes the one or more chemical reactants to undergo a chemical reaction having a reaction rate that is at least 25% greater than the reaction rate for a chemical reaction under similar conditions, without the presence of the nanomaterial.

15. The method of claim 14, wherein the reaction rate is approximately 200% greater than the reaction rate for a chemical reaction under similar conditions, without the presence of the nanomaterial.

16. The method of claim 12, wherein the reaction comprises a hydroxylation reaction.

17. The method of claim 12, wherein one of the one or more chemical reactants comprises coumarin carboxylic acid.

18. The method of claim 12, wherein the nanoparticle is coated with polyethylene glycol ("PEG") ligands.

19. The method of claim 12, wherein the dose rate is about 20 Gy/min.

* * * * *